US010881788B2

(12) United States Patent
Dang et al.

(10) Patent No.: US 10,881,788 B2
(45) Date of Patent: Jan. 5, 2021

(54) DELIVERY DEVICE INCLUDING REACTIVE MATERIAL FOR PROGRAMMABLE DISCRETE DELIVERY OF A SUBSTANCE

(71) Applicant: International Business Machines Corporation, Armonk, NY (US)

(72) Inventors: Bing Dang, Chappaqua, NY (US); Gregory M Fritz, Wakefield, MA (US); Eric P Lewandowski, Morristown, NJ (US); Joana S. B. T. Maria, New York, NY (US); Bucknell C Webb, Yorktown Heights, NY (US); Steven L Wright, Cortlandt Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/928,508

(22) Filed: Oct. 30, 2015

(65) Prior Publication Data
US 2017/0119960 A1    May 4, 2017

(51) Int. Cl.
*A61M 5/142* (2006.01)

(52) U.S. Cl.
CPC .......... *A61M 5/14276* (2013.01); *A61M 2205/0244* (2013.01); *A61M 2205/0277* (2013.01); *A61M 2205/04* (2013.01)

(58) Field of Classification Search
CPC .......... A61M 5/14276; A61M 2205/04; A61M 2205/0244; A61M 2205/077; A61M 5/16804; A61M 2205/3561; A61M 5/44; A61M 5/172; A61M 2205/332;
(Continued)

(56) References Cited

U.S. PATENT DOCUMENTS

| 3,993,071 A | 11/1976 | Higuchi et al. |
| 4,917,895 A | 4/1990 | Lee et al. |
| 4,941,205 A | 7/1990 | Horst et al. |

(Continued)

FOREIGN PATENT DOCUMENTS

| CN | 201725352 | 1/2011 |
| CN | 202600746 | 12/2012 |

(Continued)

OTHER PUBLICATIONS

Hu et al., "A composite thermo-responsive membrane system for improved controlled-release", Journal of Chemical Engineering and Technology 30.4 on Apr. 1, 2007,: pp. 523-529 (p. 523 only).

(Continued)

*Primary Examiner* — William R Carpenter
*Assistant Examiner* — Hamza A Darb
(74) *Attorney, Agent, or Firm* — L. Jeffrey Kelly; Otterstedt, Wallace & Kammer, LLP

(57) ABSTRACT

A digital biomedical device includes a substrate forming a cavity, a seal formed around the cavity, a lid coupled to the substrate by the seal, a reactive metal structure comprising a plurality of metal layers, wherein the reactive metal structure is a component of at least one of the substrate and the lid, a metal trace configured to initiate a self-propagating reaction between the plurality of metal layers of the reactive metal structure and release contents of the cavity, and a power supply configured to apply an electric current to the metal trace.

14 Claims, 10 Drawing Sheets

(58) Field of Classification Search
CPC .......... A61M 2207/00; A61M 2205/50; A61K 9/0097; B81B 7/02
See application file for complete search history.

(56) References Cited

U.S. PATENT DOCUMENTS

| | | | |
|---|---|---|---|
| 5,366,454 A | 11/1994 | Currie et al. | |
| 5,474,529 A | 12/1995 | Arenberg | |
| 5,606,323 A | 2/1997 | Heinrich et al. | |
| 5,912,632 A | 6/1999 | Dieska et al. | |
| 6,068,853 A | 5/2000 | Giannos et al. | |
| 6,243,013 B1 | 6/2001 | Duan et al. | |
| 6,334,859 B1 | 1/2002 | Richter | |
| 6,436,853 B2 | 8/2002 | Lin et al. | |
| 6,551,838 B2 | 4/2003 | Santini, Jr. et al. | |
| 6,593,845 B1 | 7/2003 | Friedman et al. | |
| 6,703,921 B1 | 3/2004 | Wuidart et al. | |
| 6,773,429 B2 | 8/2004 | Sheppard, Jr. et al. | |
| 6,831,548 B1 | 12/2004 | Eber et al. | |
| 6,849,463 B2 | 2/2005 | Santini, Jr. et al. | |
| 6,875,208 B2 | 4/2005 | Santini, Jr. et al. | |
| 6,953,455 B2* | 10/2005 | Cho ................... | A61K 9/0024 604/890.1 |
| 6,969,382 B2 | 11/2005 | Richter | |
| 7,001,372 B2 | 2/2006 | Richter | |
| 7,070,592 B2 | 7/2006 | Santini, Jr. et al. | |
| 7,114,312 B2 | 10/2006 | Coppeta et al. | |
| 7,226,442 B2 | 6/2007 | Sheppard, Jr. et al. | |
| 7,260,371 B1 | 8/2007 | Yones | |
| 7,372,359 B2 | 5/2008 | Wuidart et al. | |
| 7,455,667 B2 | 11/2008 | Uhland et al. | |
| 7,473,248 B2 | 1/2009 | Santini, Jr. et al. | |
| 7,510,551 B2 | 3/2009 | Uhland et al. | |
| 7,534,241 B2 | 5/2009 | Coppeta et al. | |
| 7,563,255 B2 | 7/2009 | Adamis et al. | |
| 7,587,190 B2 | 9/2009 | Balachandran et al. | |
| 7,598,864 B2 | 10/2009 | Sugimura et al. | |
| 7,642,918 B2 | 1/2010 | Kippelen et al. | |
| 7,652,313 B2 | 1/2010 | Ellis-Monaghan et al. | |
| 7,652,557 B2 | 1/2010 | Kantrowitz et al. | |
| 7,791,481 B2 | 9/2010 | Landt et al. | |
| 7,901,397 B2 | 3/2011 | Santini, Jr. et al. | |
| 7,910,151 B2 | 3/2011 | Uhland et al. | |
| 7,983,565 B2 | 7/2011 | Varshneya et al. | |
| 8,083,710 B2 | 12/2011 | Hood et al. | |
| 8,095,197 B2 | 1/2012 | Santini, Jr. et al. | |
| 8,205,800 B2 | 6/2012 | Addy | |
| 8,211,092 B2 | 7/2012 | Uhland et al. | |
| 8,273,610 B2 | 9/2012 | Dr-Bach et al. | |
| 8,369,786 B2 | 2/2013 | Witschnig et al. | |
| 8,477,015 B1 | 7/2013 | Pai | |
| 8,924,023 B2 | 12/2014 | Akpan | |
| 9,042,281 B2 | 5/2015 | Miller et al. | |
| 9,055,902 B2 | 6/2015 | Liu | |
| 9,108,006 B2 | 8/2015 | Jensen et al. | |
| 9,734,371 B2 | 8/2017 | Friedman et al. | |
| 9,755,701 B2 | 9/2017 | Friedman et al. | |
| 9,937,124 B2 | 4/2018 | Chey et al. | |
| 10,007,819 B2 | 6/2018 | Friedman et al. | |
| 10,090,889 B2 | 10/2018 | Friedman et al. | |
| 10,255,467 B2 | 4/2019 | Friedman et al. | |
| 10,286,198 B2 | 5/2019 | Dang et al. | |
| 2001/0004236 A1 | 6/2001 | Letkomiller et al. | |
| 2001/0051766 A1 | 12/2001 | Gazdzinski | |
| 2003/0175354 A1 | 9/2003 | Drizen et al. | |
| 2003/0198474 A1 | 10/2003 | Mooney et al. | |
| 2004/0020173 A1 | 2/2004 | Cho | |
| 2004/0062556 A1 | 4/2004 | Kubo et al. | |
| 2004/0106914 A1* | 6/2004 | Coppeta ................ | A61K 9/0004 604/892.1 |
| 2004/0106953 A1* | 6/2004 | Yomtov ............ | A61M 5/14276 607/3 |
| 2004/0166140 A1 | 8/2004 | Santini, Jr. et al. | |
| 2004/0230182 A1 | 11/2004 | Heruth et al. | |
| 2005/0001724 A1 | 1/2005 | Heinrich et al. | |
| 2005/0050859 A1 | 3/2005 | Coppeta et al. | |
| 2005/0055014 A1 | 3/2005 | Coppeta et al. | |
| 2005/0061870 A1 | 3/2005 | Stockton | |
| 2005/0096587 A1* | 5/2005 | Santini, Jr. .......... | A61B 5/1486 604/66 |
| 2005/0143715 A1 | 6/2005 | Cima et al. | |
| 2005/0152261 A1 | 7/2005 | Kahlman | |
| 2005/0206504 A1 | 9/2005 | Sugimura et al. | |
| 2005/0240370 A1 | 10/2005 | Diorio et al. | |
| 2006/0105275 A1 | 5/2006 | Maloney et al. | |
| 2006/0115323 A1* | 6/2006 | Coppeta ................ | A61K 9/0097 403/270 |
| 2006/0127097 A1 | 6/2006 | Obrea et al. | |
| 2006/0222134 A1 | 10/2006 | Eldredge et al. | |
| 2006/0248576 A1 | 11/2006 | Levinson | |
| 2006/0284770 A1 | 12/2006 | Jo et al. | |
| 2007/0015549 A1 | 1/2007 | Hernandez et al. | |
| 2007/0050683 A1 | 3/2007 | Attinella et al. | |
| 2007/0096880 A1 | 5/2007 | Nagai | |
| 2007/0103311 A1 | 5/2007 | Kippelen et al. | |
| 2007/0230322 A1 | 10/2007 | Morita | |
| 2007/0253137 A1 | 11/2007 | Maloney | |
| 2007/0273485 A1 | 11/2007 | Balachandran et al. | |
| 2008/0042043 A1 | 2/2008 | Reime et al. | |
| 2008/0088417 A1 | 4/2008 | Smith et al. | |
| 2008/0094245 A1 | 4/2008 | Hardacker et al. | |
| 2008/0154230 A1 | 6/2008 | Subramony et al. | |
| 2008/0231458 A1 | 9/2008 | Fein | |
| 2008/0244273 A1 | 10/2008 | Chen et al. | |
| 2009/0099553 A1 | 4/2009 | Langereis et al. | |
| 2009/0202254 A1 | 8/2009 | Majumdar et al. | |
| 2009/0294535 A1 | 12/2009 | Paeschke et al. | |
| 2009/0306633 A1 | 12/2009 | Trovato et al. | |
| 2010/0061734 A1 | 3/2010 | Knapp | |
| 2010/0128749 A1 | 5/2010 | Amann et al. | |
| 2010/0182160 A1 | 7/2010 | Lu | |
| 2010/0328043 A1 | 12/2010 | Jantunen et al. | |
| 2011/0053503 A1 | 3/2011 | Witschnig et al. | |
| 2011/0108616 A1 | 5/2011 | Wang | |
| 2011/0163852 A1 | 7/2011 | Kanda et al. | |
| 2011/0188800 A1 | 8/2011 | Futami | |
| 2011/0205134 A1 | 8/2011 | Blumberg, Jr. | |
| 2011/0215156 A1 | 9/2011 | Johnson, II et al. | |
| 2011/0318013 A1 | 12/2011 | Primm | |
| 2012/0013446 A1 | 1/2012 | Ino | |
| 2012/0032785 A1 | 2/2012 | Kamata | |
| 2012/0153910 A1 | 6/2012 | Bulzacchelli et al. | |
| 2012/0161338 A1 | 6/2012 | Lowenthal et al. | |
| 2012/0234922 A1 | 9/2012 | Sample et al. | |
| 2012/0245565 A1 | 9/2012 | Shachar et al. | |
| 2012/0294625 A1 | 11/2012 | Dynes et al. | |
| 2013/0030763 A1 | 1/2013 | Mazzillo | |
| 2013/0106607 A1 | 5/2013 | Clement et al. | |
| 2013/0206837 A1 | 8/2013 | Szu | |
| 2013/0216219 A1 | 8/2013 | Honda et al. | |
| 2013/0285795 A1 | 10/2013 | Virtanen et al. | |
| 2014/0015642 A1 | 1/2014 | White | |
| 2014/0016945 A1 | 1/2014 | Pan | |
| 2014/0022057 A1 | 1/2014 | Trosper | |
| 2014/0296773 A1 | 10/2014 | Bulent et al. | |
| 2014/0332663 A1 | 11/2014 | Zecri | |
| 2015/0102908 A1 | 4/2015 | Griesmann et al. | |
| 2015/0162984 A1 | 6/2015 | Liu et al. | |
| 2015/0227766 A1 | 8/2015 | Koezuka et al. | |
| 2015/0272830 A1 | 10/2015 | Iordanov et al. | |
| 2015/0310715 A1 | 10/2015 | Nekoogar et al. | |
| 2015/0382425 A1 | 12/2015 | Lewis et al. | |
| 2016/0074323 A1 | 3/2016 | Chey et al. | |
| 2016/0117583 A1 | 4/2016 | Butler et al. | |
| 2016/0119059 A1 | 4/2016 | Chandra et al. | |
| 2016/0242124 A1 | 8/2016 | Zhou et al. | |
| 2016/0292470 A1 | 10/2016 | Friedman et al. | |
| 2016/0294481 A1 | 10/2016 | Friedman et al. | |
| 2017/0105260 A1 | 4/2017 | Ho et al. | |
| 2017/0119960 A1 | 5/2017 | Dang et al. | |
| 2017/0140182 A1 | 5/2017 | Mizuno | |
| 2017/0147915 A1 | 5/2017 | Butler et al. | |
| 2017/0228568 A1 | 8/2017 | Friedman et al. | |

(56) References Cited

U.S. PATENT DOCUMENTS

2017/0272125 A1 9/2017 Friedman et al.
2017/0325746 A1 11/2017 Niichel et al.
2018/0133152 A1 5/2018 Chey et al.

FOREIGN PATENT DOCUMENTS

| CN | 202711296 | 1/2013 |
|---|---|---|
| CN | 203562013 | 4/2014 |
| CN | 103955736 | 7/2014 |
| DE | 102016204669 | 10/2016 |
| JP | 2013061888 | 4/2013 |
| KR | 20090098472 | 9/2009 |
| WO | WO2008091826 | 7/2008 |
| WO | WO2009064402 | 5/2009 |
| WO | WO2009107136 | 9/2009 |

OTHER PUBLICATIONS

Fritz et al. "Thresholds for igniting exothermic reactions in Al/Ni multilayers using pulses of electrical, mechanical, and thermal energy," J. Appl. Phys. 113, 014901, Jan. 2013, pp. 1-11.
Maloney et al, "Electrothermally activated microchips for implantable drug delivery and biosensing," Journal of Controlled Release 109 (Nov. 8, 2005) pp. 244-255.
Roy et al., RFID: From Supply Chains to Sensor Nets, Proceedings of the IEEE, Jul. 2010, pp. 1583-1592, vol. 98, No. 3.
Buckner et al., GPS and Sensor-Enabled RFID Tags, Unclassified Document, Oak Ridge National Laboratory, http://www.oml.gov/webworks/cppr/y2001/pres/118169.pdf, 2001, 5 pages.
Sample et al., Design of a passively-powered, programmable sensing platform for UHF RFID systems. In 2007 IEEE International Conference on RFID, pp. 149-156, IEEE, Mar. 2007.
E.E. Nuxoll et al., "BioMEMS Devices for Drug Delivery," IEEE Engineering in Medicine and Biology Magazine, Jan./Feb. 2009, pp. 31-39.
Knowles, "New Product: Ultrasonic MEMS Microphone," http://www.knowles.com/eng/Newsroom/New-product-Ultrasonic-MEMS-Microphone, Feb. 1, 2016, 2 pages.
R. Colin Johnson, "MEMS Mics Taking Over, Tasks Once Performed by Specialized Chips," EETimes, http://www.eetimes.com/document.asp?doc_id=1324827, Dec. 2, 2014, 3 pages.
Focused Ultrasound Foundation, "Overview," http://www.fusfoundation.org/the-technology/overview, Feb. 1, 2016, 2 pages.
J. M. Maloney et al., "Electrothermally Activated Microchips for Implantable Drug Delivery and Biosensing," Science Direct, Journal of Controlled Release vol. 109, Issues 1-3, Dec. 2005, pp. 244-255.
L. Hu et al., "A Composite Thermo-Responsive Membrane System for Improved Controlled-Release," Chemical Engineering & Technology, vol. 30, No. 4, 2007, pp. 523-529.
Fritz et al., "Thresholds for Igniting Exothermic Reactions in Al/Ni Multilayers Using Pulses of Electrical, Mechanical, and Thermal Energy," Jorunal of Applied Physics, vol. 113, No. 1, 2013, 12 pages.
Paul J. Otterstedt, List of IBM Patents or Patent Applications Treated as Related, Aug. 10, 2020, pp. 1-2.

* cited by examiner

DELIVERY DEVICE INCLUDING REACTIVE MATERIAL FOR PROGRAMMABLE DISCRETE DELIVERY OF A SUBSTANCE

BACKGROUND

The present disclosure relates to devices for delivering substances, and more particularly to a biomedical device having controllable seals formed on a reactive material.

Biomedical devices are typically implanted into, worn on, or otherwise inserted in the body. The functions of a biomedical device can include medication delivery, sensor activation, sensor data collection and analysis, etc.

Digital biomedical devices, such as controlled release devices, medication delivery and bio-sensing devices based on MEMS (MicroElectro-Mechanical-Systems) technology, etc., typically use electricity to generate heat and melt a membrane in order to open a reservoir. These devices are typically limited by battery capacity.

BRIEF SUMMARY

According to an exemplary embodiment of the present invention, a digital biomedical device comprising a substrate forming a cavity, a seal formed around the cavity, a lid coupled to the substrate by the seal, a reactive metal structure comprising a plurality of metal layers, wherein the reactive metal structure is a component of at least one of the substrate and the lid, a metal trace configured to initiate a self-propagating reaction between the plurality of metal layers of the reactive metal structure and release contents of the cavity, and a power supply configured to apply an electric current to the metal trace.

According to an exemplary embodiment of the present invention, in a digital biomedical device comprising a substrate forming a cavity, a seal formed around the cavity, and a lid coupled to the substrate by the seal, a method of activating the device comprises initiating a self-propagating reaction in a reactive metal structure by applying an electric current to the reactive metal structure comprising a plurality of metal layers, wherein the reactive metal structure is a component of at least one of the substrate and the lid, and exposing contents of the cavity to an exterior of the digital biomedical device upon the self-propagating reaction of the reactive metal structure.

BRIEF DESCRIPTION OF THE SEVERAL VIEWS OF THE DRAWINGS

Preferred embodiments of the present invention will be described below in more detail, with reference to the accompanying drawings.

DETAILED DESCRIPTION

According to an exemplary embodiment of the present invention, a digital biomedical device includes a reactive metal structure, wherein the digital biomedical device is configured to be activated, initiating a reaction of the reactive metal structure at low temperature and with low energy. According to an exemplary embodiment of the present invention, the digital biomedical device comprises a plurality of discrete, electronically-addressable structures (e.g., cavities or reservoirs). The electronically-addressable structures can be disposed in an array.

In one or more embodiments, the digital biomedical device includes a plurality of reservoirs containing a substance, such as an active agent, chemical or medication, which can be controllably released. In other embodiments, the digital biomedical device includes a plurality of cavities containing sensors for chemical activation or exposure. Each electronically-addressable structure is sealed with an electrically activated membrane or lid structure. The membrane or lid structure can be partially or completely opened under the control of the digital biomedical device.

Figure 1:
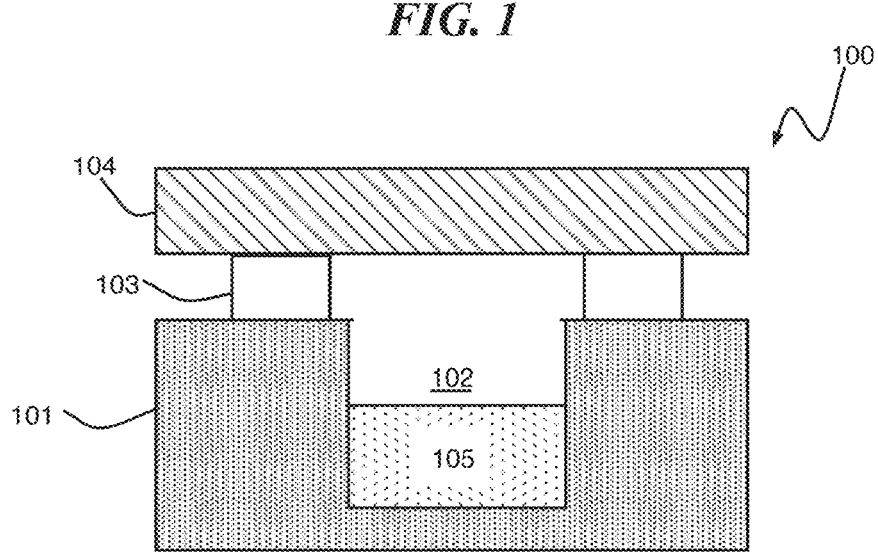
FIG. 1 shows a reactive material based releasable seal according to an exemplary embodiment of the present invention.

FIG. 1 shows a delivery device 100 comprising reactive material based releasable seal according to one or more embodiments of the present invention. The delivery device 100 includes a substrate 101 having a cavity 102, a seal 103 and a lid 104. The seal 103 can be formed of a solder, oxide bonding or a polymer adhesive. A substance, such as an active agent 105, can be held in the cavity 102. According to at least one embodiment of the present invention, the seal 103 adheres the lid 104 to the substrate 101, thereby isolating the contents of the electronically-addressable structures (e.g., reservoirs) from the surrounding environment.

According to one or more embodiments of the present invention, the mechanism for releasing the contents of the cavity 102 depends on an implementation of a reactive material. For example, in one exemplary embodiment, the lid 104 includes a membrane formed of a reactive material. In another exemplary embodiment the lid 104 is released when a reactive material compromises the integrity of the seal 103. These and other embodiments are described herein.

Figure 4:
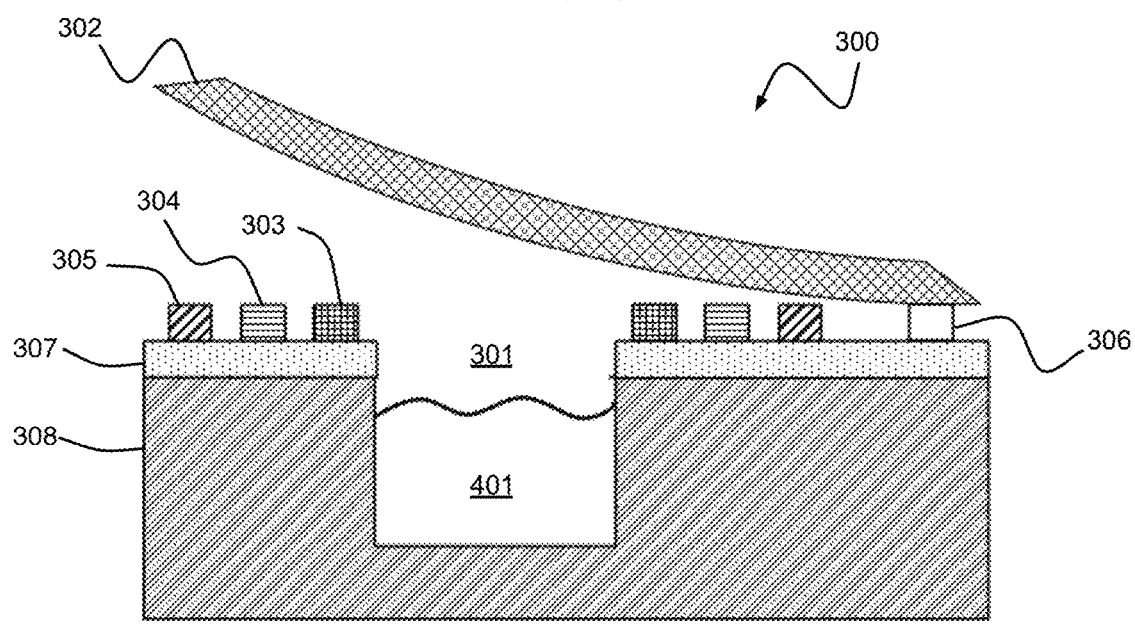
FIG. 4 is a cross section of the digital biomedical device of FIG. 3 according to an exemplary embodiment of the present invention.

In at least one embodiment of the present invention, the lid 104 is tethered in a stressed state (e.g., see FIG. 4). In another embodiment, the lid 104 is a non-tethered flat releasable structure (e.g., see FIG. 2). The type of lid can depend on the application, for example, for use in vivo the lid 104 is formed of a bio-compatible and/or bio-degradable materials.

Ignition of the reactive material can be initiated via a resistive heater, a high current density electric pulse, etc. In at least one embodiment of the present invention, the active agent 105 is released when a membrane is melted by the heat of reaction in the reactive material. In at least one embodiment of the present invention, the lid 104 is released upon activation of the delivery device and a phase change of the reactive material. In at least one embodiment, the phase change occurs without melting and/or vaporizing the membrane. In at least one embodiment, the phase change results in a change in membrane density, thereby introducing/relieving stress in the lid 104. In at least one embodiment, stress in the lid 104 is relieved with the formation of cracks that allow the active agent 105 to permeate a membrane component of the lid 104 and exit the delivery device 100. In another embodiment, as determined by the design of the structure, stress in the lid 104 is relieved by strain and shear (e.g., delamination) of an interface between a membrane component of the lid 104 and the seal 103, or by shear of the interface between the seal 103 and the substrate 101 including a membrane formed of a reactive material.

It should be understood that the lid structure is an overall structure, which encloses the cavity. Furthermore, the lid can include the membrane formed of the reactive material. In at least one embodiment, the membrane includes a reactive metal structure and is formed as a component of a substrate disposed adjacent to a seal.

Figure 2:
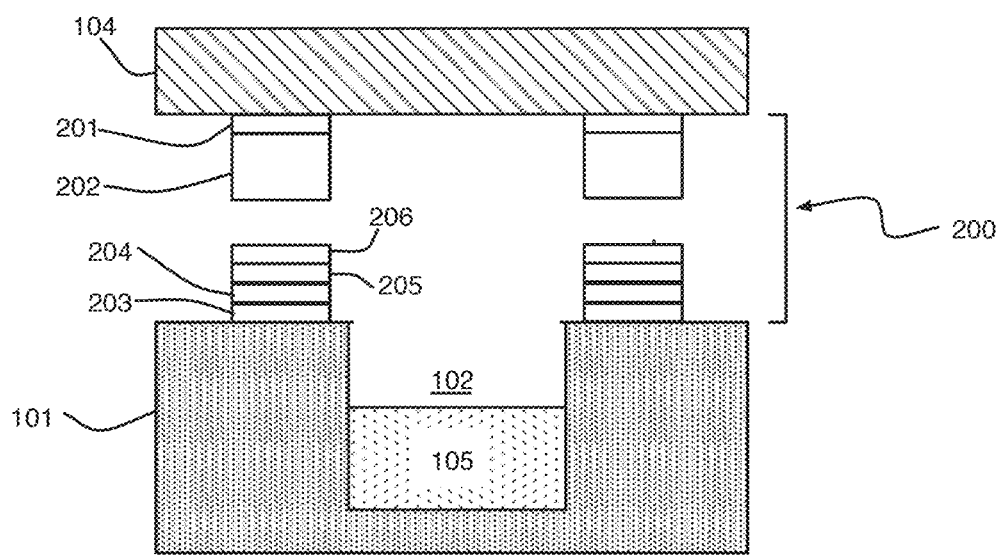
FIG. 2 shows a layered structure for connecting the membrane to a substrate according to an exemplary embodiment of the present invention.

FIG. 2 shows a layered structure 200 for connecting the lid 104 to the substrate 101. A first layer 201, comprising a metal or adhesion layer, is formed on the lid 104. A second layer 202 (e.g., a solder, polymer or oxide) is formed on the first layer 201. A first metal or adhesion layer 203, a reactive material layer 204, an insulator layer 205 (e.g., silicon dioxide ($SiO_2$)) and a second a second solder or adhesion layer 206 are sequentially formed on the substrate 101, which can be a silicon (Si) substrate. According to an exemplary embodiment of the present invention, the insulator layer 205 restricts heat flow from the reactive material layer 204 into the lid 104, or in the case of electrical activation, restricts an electrical current from flowing into the lid 104. In at least one embodiment, if sufficient heat is generated in activation of the reactive material 204, such that heat loss into the lid 104 does not prevent self-propagation of the reaction in layer 204, then insulator layer 205 can be omitted.

The digital biomedical device according to an embodiment of the present invention is configured for controlled-release of the active agent. Controlled release can refer to a release time of the active agent, a release rate, or both. In at least one embodiment of the present invention, the controlled release is a sustained/continuous release of the active agent over a period of time (e.g., one hour, 12, hours, multiple days). Such a controlled release can be applied for cancer treatment, pain management, hypertension, angina, etc. In one or more embodiments of the present invention, the controlled release is a pulsatile release of discrete amounts of drug at variable time intervals. Such a controlled release can be applied for delivery of an active agent that mimics the way the body produces some compounds like growth hormone and insulin.

According to an exemplary embodiment of the present invention, a reactive metal material includes two or more alternating dissimilar layers of metallic elements. Table 1 shows exemplary combinations of layers to form a reactive material.

TABLE 1

| Reactants | Adiabatic $T_{max}$ (° C.) | State of Product | Heat of Reaction (cal/g) | (cal/cc) |
|---|---|---|---|---|
| Si + 2B | 230 | Solid | 76.4 | 177 |
| Cu + Pd | 600 | Solid | 44.5 | 472 |
| Al + Ti | 1324 | Solid | 240 | 872 |
| Si + Co | 1460 | Solid-Liquid | 299 | 1450 |
| Al + Ni | 1638 | Solid | 330 | 1710 |
| Al + Pt | 2800 | Liquid | 216 | 2510 |
| Al + Pd | 2380 | Liquid | 327 | 2890 |

Known methods for forming the layers of reactive metals can be used. These include rolling thick laminated layers into thin sheets, evaporation or sputtering of thin film layers onto a substrate, etc. For a suitable combination of materials, layer thickness and structure, the metals undergo an exothermic, self-propagating reaction upon application of a stimulus. To enable a reaction with good energy release and self-propagation, the layers are formed with low or no intermixing or diffusion between layers during fabrication. According to an embodiment of the present invention, the layers are thin, without being intermixed, to reduce the energy needed to initiate a reaction. According to an embodiment of the present invention, for typical deposition technologies, the thickness of the individual layers is between about 5 nanometers (nm) and 50 nm, and preferably greater than about 10 nm to avoid intermixing and reaction during layer deposition. The reactive metal material reaction can be initiated by electrical, magnetic, optical, thermal or mechanical means. For example, in at least one embodiment, the reactive metal material is heated by passing an electric current through a heater electrode disposed in close proximity to the reactive metal. In another example, the electric current is passed through the reactive metal itself. In yet another example, external methods of heating can be used including inductive heating, radiative heating, and mechanical shock. The dependence of ignition energy on layer thickness for the reactive material system aluminum (Al)+nickel (Ni) was studied by Fritz et al. (J. Applied Physics 113, 014901 (2013)), and a thermal ignition temperature as low as 232° C. was obtained for a bilayer thickness of 30 nm.

In the exemplary case of a reactive material formed of Al and palladium (Pd), the reaction is about 3 times larger than the energy needed to bring the individual components up to a melting temperature of the alloy, or to melt the alloy itself. Since the ignition temperature is relatively low, the ignition energy can be about 5-10 times smaller than that needed to melt the structure, assuming uniform heating of the entire structure.

In the case that the reactive materials Al and Pd are thermally isolated, only about 1% of the volume of material needs to be heated to the ignition temperature to initiate a self-propagating reaction. With localized heating, the ignition energy can be about 500-1000 times less than that needed to melt the components of the structure. Assuming 1% volume heating, the released energy can be in the range 1500-3000 times larger than the ignition energy.

According to an exemplary embodiment of the present invention, the membrane is an activated porous membrane structure. The activated porous membrane structure is a composite structure including two or more components. At least a first component is a mechanical support structure. In one or more embodiments, the mechanical support structure is an insulating material, such as $SiO_2$ or silicon nitride (SiNx). In one or more embodiments, the mechanical support structure includes multiple vias. According to at least one embodiment of the present invention, the vias are filled or sealed with a second component comprising a reactive metal material. According to at least one embodiment of the present invention, upon activation, the reactive metal material is compromised (e.g., melted, removed, opened, permeated, etc.), while the support structure remains intact. After activation, the membrane allows a substance to pass (e.g., a medication or chemical), and/or exposes a sensor contained within an underlying structure to the surrounding environment.

A digital biomedical device according to an embodiment of the present invention comprises a membrane formed as a reactive metal structure and configured to initiate a reaction at low temperature with low energy needs. For example, for a certain type of lid, the electrical energy needed to open an underlying structure (i.e., compromise the reactive metal material) is less than about 1 microjoule ($\mu J$).

According to at least one embodiment of the present invention, for a membrane comprising two reactive materials formed of thin layers of Al and Pd, the layers can be made to react to release about 90 kilojoule (kJ)/mole of energy. For films of 50×50 microns and 1 μm thickness, the released heat energy for a Al+Pd structure would be about 30 μJ. This energy is larger than that needed to melt the individual components under adiabatic conditions (about 12 μJ), or that needed to melt an AlPd alloy (about 12.7 μJ).

According to at least one embodiment of the present invention, the energy needed to heat an entire Al+Pd membrane with dimensions 50×50×1 micrometer (μm) to an ignition temperature of 250° C. is about 1.8 μJ. Additionally, the Al+Pd membrane can be locally triggered, which substantially reduces a total energy needed to start the reaction. According to at least one embodiment of the present invention, the reaction continues in a self-propagation manner until the Al and Pd reactants are consumed and the stored chemical energy is released.

Figure 3:
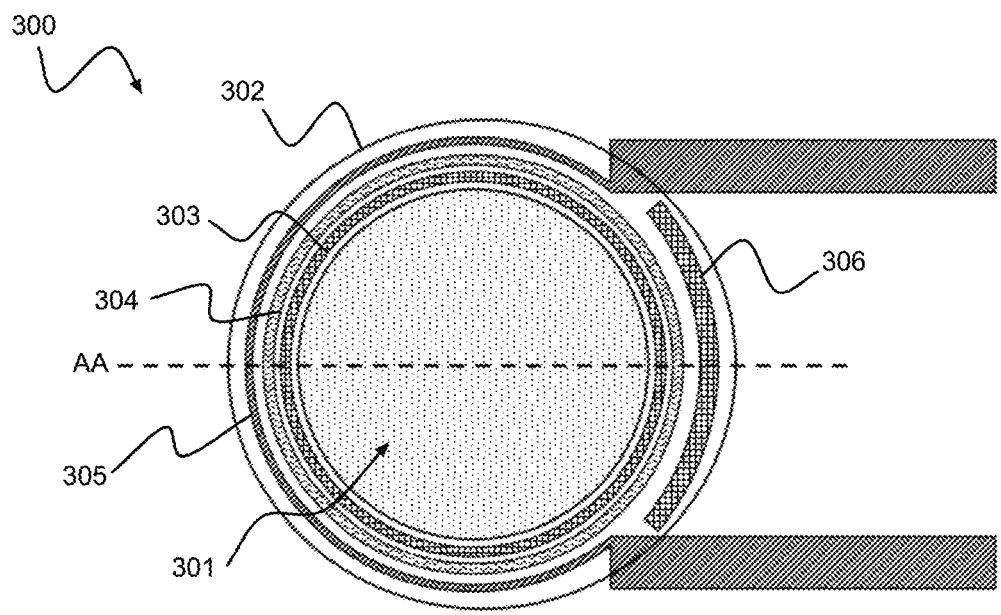
FIG. 3 is a diagram of a digital biomedical device according to an exemplary embodiment of the present invention.

Referring to FIG. 3, a digital biomedical device 300 according to an embodiment of the present invention includes a cavity 301 surrounded by a stressed lid 302 enveloping a cavity seal 303, reactive metal layers 304, heater electrode 305 and hinge 306. The cavity 301 is formed in a substrate formed of, for example, a first layer 307 of $SiO_2$ formed on a second layer 308 of Si.

The release of the cavity seal 303 can be initiated by heat generated by the heater electrode 305 initiating and propagating an exothermic reaction in layer 304. In at least one embodiment, the heat generated from heater electrode 305 and reactive metal layers 304 combine to melt or degrade the cavity seal 303, thereby releasing the stressed lid 302. In a suitably-designed structure, the heat is substantially confined to the region containing the reactive metal layers 304 and cavity seal 303 such that the stressed lid 302 adhesion to the hinge structure 306 remains intact.

In at least one embodiment, the digital biomedical device is formed wherein the stressed lid 302 comprises a membrane composed of reactive material. In this case, a patterned electrode structure can be used to provide heat to the stressed lid 302 to ignite the reactive material.

FIG. 4 is a cross-section of FIG. 3 along line AA in an open state, with an active agent 401 disposed within the cavity 301. According to one or more embodiments of the present invention, the lid is a stressed structure that curls when the cavity seal 303 is opened.

According to an exemplary embodiment of the present invention, the layered structure is electrically conductive, bio-compatible and generates little or no gas during a reaction. The reactive layers can melt or fracture the cavity seal or fracture themselves. The reactive layers both get hot and undergo dimensional changes creating stress.

Figure 5:
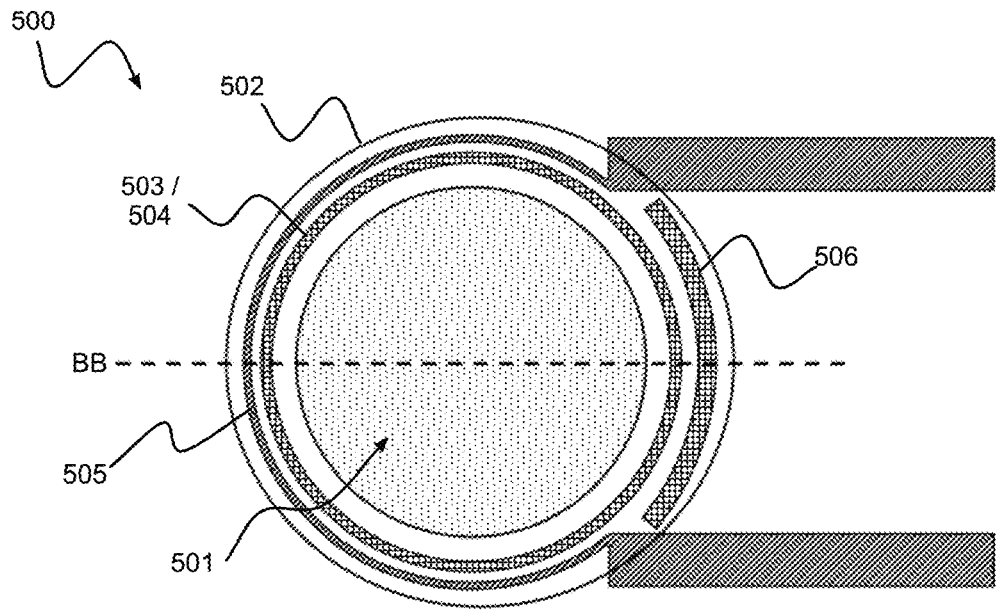
FIG. 5 is a diagram of a digital biomedical device according to an exemplary embodiment of the present invention.

Referring to FIG. 5, a digital biomedical device 500 according to an embodiment of the present invention includes a cavity 501 surrounded by a stressed lid 502. The stressed lid 502 envelopes a composite structure including a cavity seal 503 and reactive metal layers 504. The digital biomedical device 500 further includes a heater electrode 505 and hinge 506.

Figure 6:
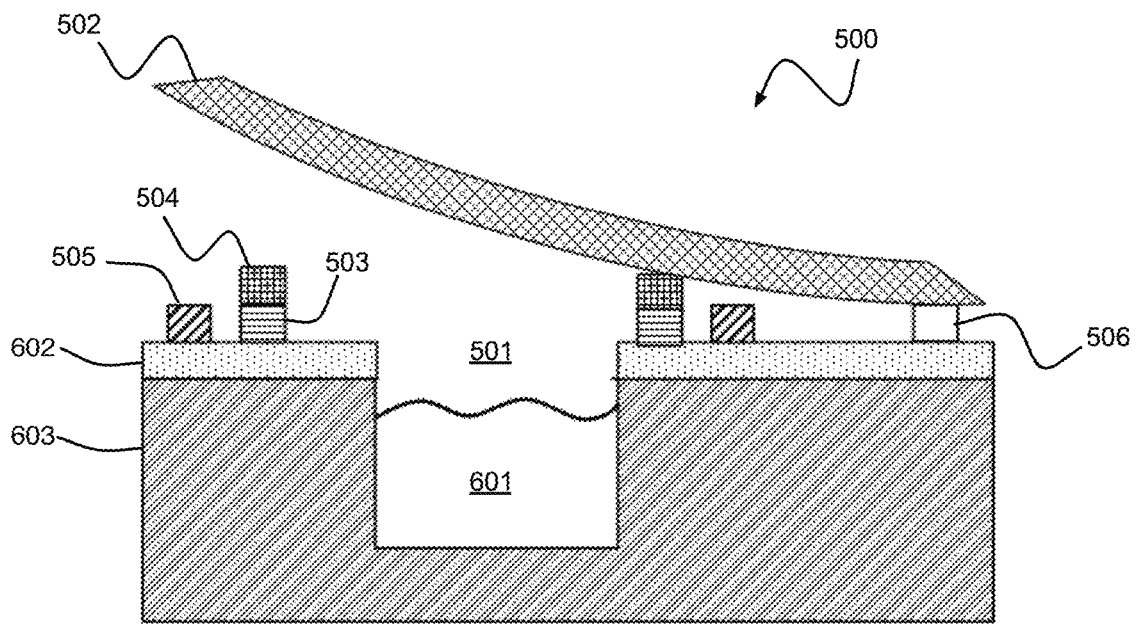
FIG. 6 is a cross section of the digital biomedical device of FIG. 5 according to an exemplary embodiment of the present invention.

FIG. 6 is a cross-section of FIG. 5 along line BB in an open state. FIG. 6 shows an active agent 601 disposed within the cavity 501. Also shown are substrate layers 602 and 603 formed of, for example, $SiO_2$ and Si, respectively.

Figure 7:
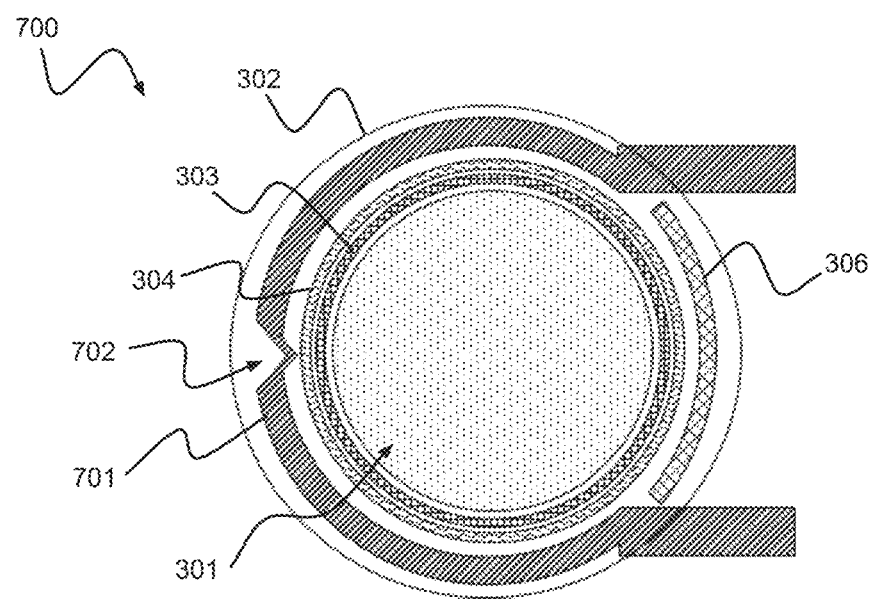
FIG. 7 is a diagram of a digital biomedical device according to an exemplary embodiment of the present invention.

Referring to FIG. 7, a digital biomedical device 700 according to an embodiment of the present invention includes a cavity 301 surrounded by a stressed lid 302 enveloping a cavity seal 303, reactive metal layers 304, heater electrode 701 and hinge 306. The heater electrode 701 is formed including one or more shaped sections, e.g., shaped section 702, for localized heating. The shaped section 702 facilitates localized heating by, for example, having smaller surface area as compared to other sections of the heater electrode 701 or having a higher electric resistance, etc. In one embodiment of the present invention, the shaped section 702 has a v-shape. It should be understood that the shaped section 702 can have other configurations and that the present invention is not limited to a v-shaped section.

Figure 8:
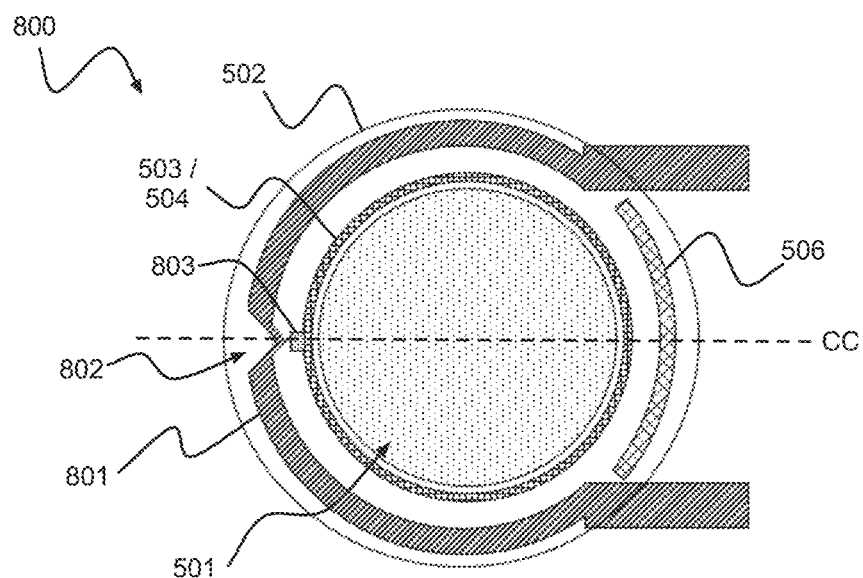
FIG. 8 is a diagram of a digital biomedical device according to an exemplary embodiment of the present invention.

Referring to FIG. 8, a digital biomedical device 800 according to an embodiment of the present invention includes a cavity 501 surrounded by a stressed lid 502. The stressed lid 502 envelopes a composite structure including a cavity seal 503 and reactive metal layers 504. The digital biomedical device 500 further includes a heater electrode 801 and hinge 506. The heater electrode 801 is formed including one or more shaped sections, e.g., shaped section 802, for localized heating. In at least one embodiment of the present invention, a reactive metal tab 803 is disposed on the composite structure and adjacent to the shaped section 802 of the heater electrode 801. In one or more embodiments, the reactive metal tab 803 facilitates local ignition of the reactive metal layers 504 of the composite structure.

Figure 9:
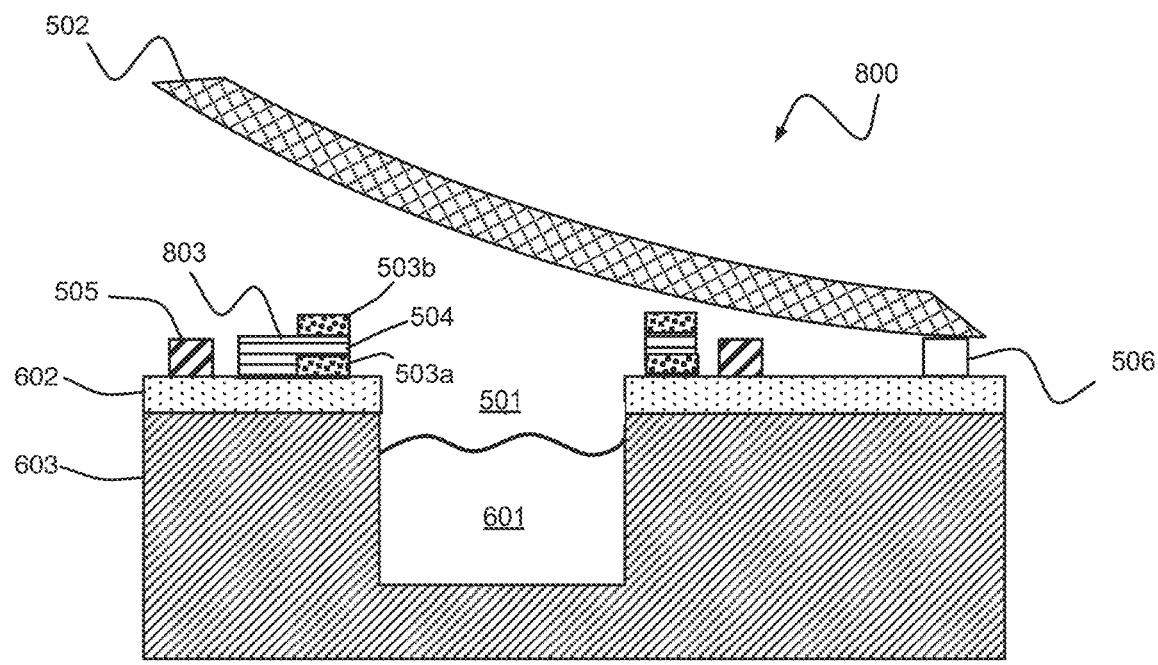
FIG. 9 is a cross section of the digital biomedical device of FIG. 8 according to an exemplary embodiment of the present invention.

FIG. 9 is a cross-section of FIG. 8 along line CC in an open state. FIG. 9 shows an active agent 601 disposed within the cavity 501, and the composite structure including first and second cavity seals 503a and 503b having the reactive metal layers 504 disposed there between. Also shown is the reactive metal tab 803. The reactive metal layers 504 can melt or fracture one or more of the cavity seals or fracture themselves, for example, when the reactive metal layers 504 heat and undergo dimensional changes creating stress.

Figure 10:
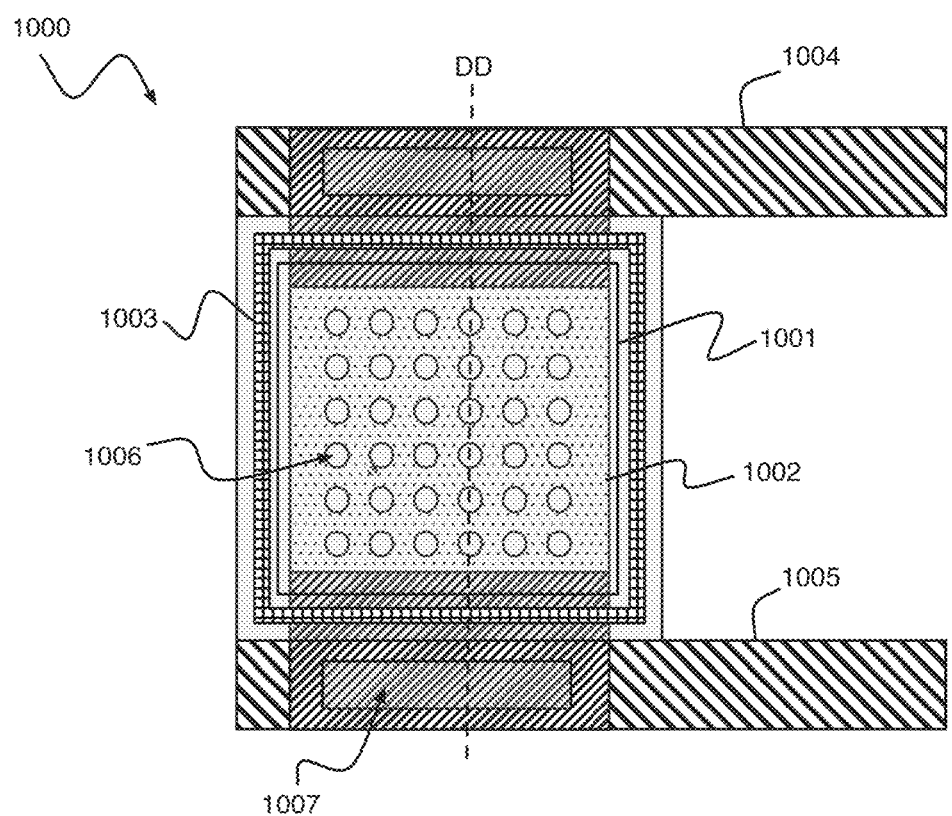
FIG. 10 is a diagram of a digital biomedical device according to an exemplary embodiment of the present invention.
Figure 11:
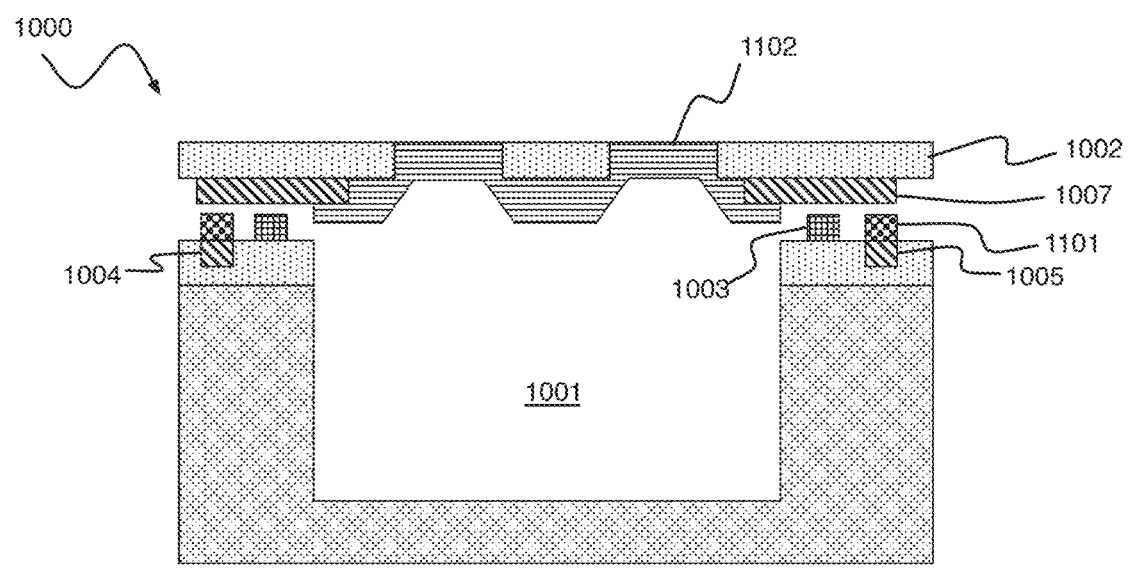
FIG. 11 is a cross section of the digital biomedical device of FIG. 10 according to an exemplary embodiment of the present invention.

Referring to FIG. 10 and FIG. 11, a digital biomedical device 1000 according to an embodiment of the present invention includes a cavity 1001 disposed under a composite lid structure comprised of a support structure 1002 and reactive metal membrane 1102. The support structure 1002 material is an electrical and thermal insulator with vias 1006 that are filled with the reactive metal membrane 1102 material. The composite lid structure is connected to a substrate (implied but not shown) by a cavity seal 1003 (e.g., an organic seal). The composite lid structure is disposed between a pair of metal traces 1004 and 1005, e.g., formed on Cu. The composite lid structure includes a metal trace 1007 connecting the reactive metal layer 1102 to the pair of metal traces 1004 and 1005 on the substrate. The composite lid structure can be compromised (e.g., to form a porous structure) by passing a current between the pair of metal traces 1004 and 1005 and through the reactive metal layer 1102. The current causes reactive metal layer 1102 to melt or vaporize, thereby clearing the vias 1006 in the support structure 1002.

FIG. 11 is a simplified cross-section of FIG. 10 along line DD, showing the cavity 1001, reactive metal membrane 1002 and cavity seal 1003. Also shown are metal traces 1004, 1005, and 1007. While an air gap is shown in FIG. 11, the cavity seal 1003 makes mechanical contact and forms a hermetic seal to both membrane 1002 and metal trace 1007. A solder 1101 can be used to make electrical connection between the metal traces 1004 and 1005 (e.g., formed of Cu) to the metal trace 1007 of the composite lid structure.

Figure 12:
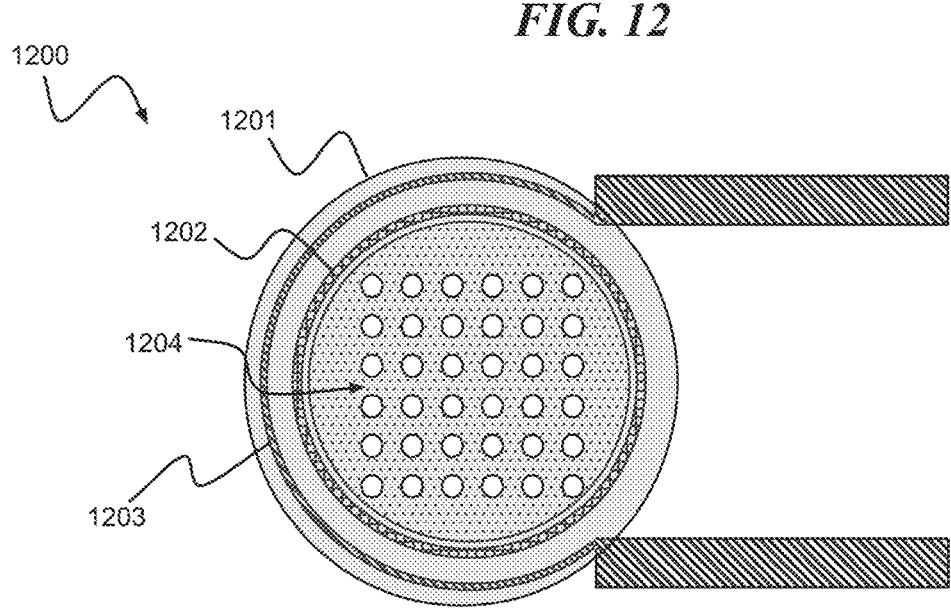
FIG. 12 is a diagram of a digital biomedical device according to an exemplary embodiment of the present invention.

Referring to FIG. 12, a digital biomedical device 1200 according to an embodiment of the present invention includes a cavity (implied by not shown) disposed under a lid including a reactive metal membrane 1201. The digital biomedical device 1200 includes a cavity seal 1202 sealing the lid including the reactive metal membrane 1201 to a substrate. The digital biomedical device 1200 further includes a heater electrode 1203. FIG. 12 is depicted with a porous membrane 1204 of the lid including the reactive metal membrane 1201 exposing the cavity below after a reaction.

Figure 13:
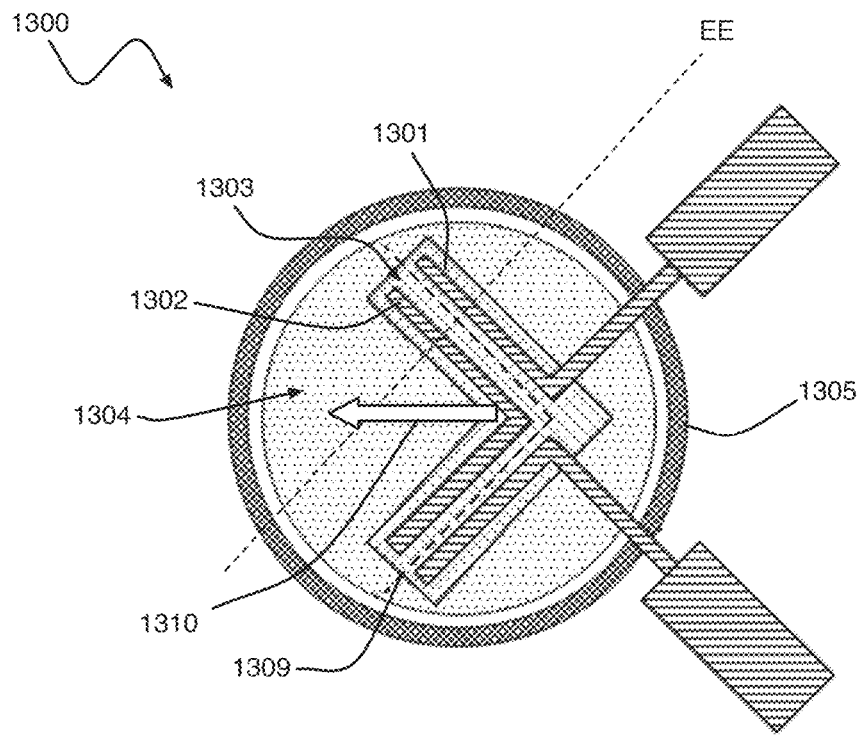
FIG. 13 is a diagram of a digital biomedical device according to an exemplary embodiment of the present invention.
Figure 14:
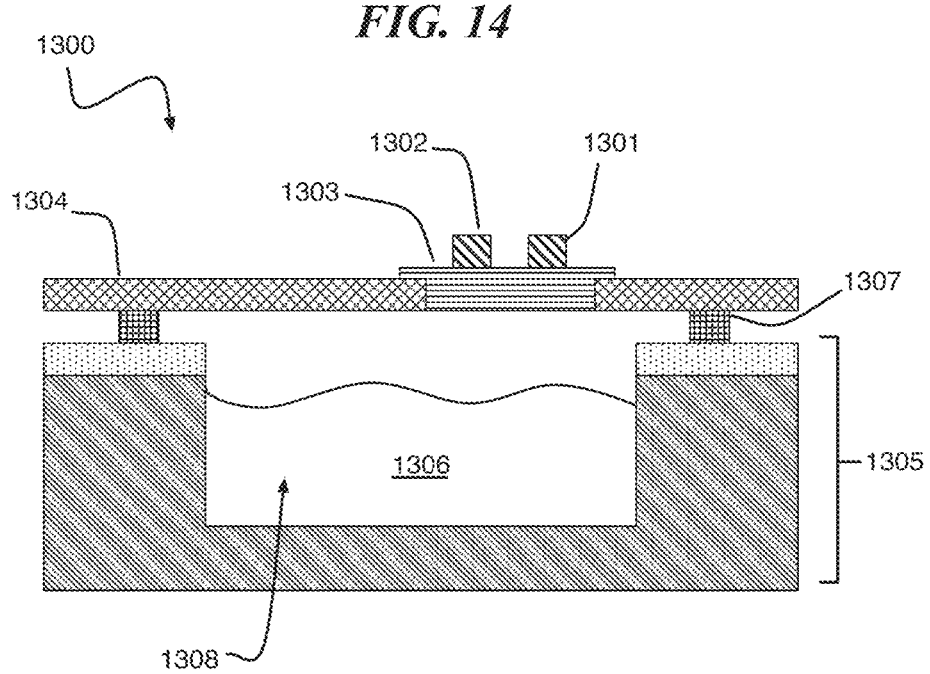
FIG. 14 is a cross section of the digital biomedical device of FIG. 13 according to an exemplary embodiment of the present invention.

FIG. 13, according to one or more embodiments of the present invention, a digital biomedical device 1300 comprises a plurality of metal traces 1301, 1302 disposed on a reactive metal structure 1303. The reactive metal structure 1303 is a component of a lid including a stressed insulator membrane 1304. The lid including the stressed insulator membrane 1304 is connected to a substrate 1305 including a cavity 1306 by a cavity seal 1307 (see FIG. 14). FIG. 14 is a cross-sectional view of the structure shown in FIG. 13 showing an active agent 1308 disposed within the cavity 1306. According to an embodiment of the present invention, the reactive metal structure 1303 ruptures upon application of a current to the metal traces, facilitating the opening of the lid including the stressed insulator membrane 1304. The rupture occurs in reactive metal structure 1303, between metal electrode structures 1301 and 1302, making a V-shaped cut in the lid including the membrane 1304 along dotted line 1309, with the stressed insulator membrane pealing in the direction of arrow 1310. The stress in the lid including the membrane 1304 is released upon the formation of the V-shaped cut by allowing the V-shaped region to peel back from the rest of the membrane structure.

Figure 15:
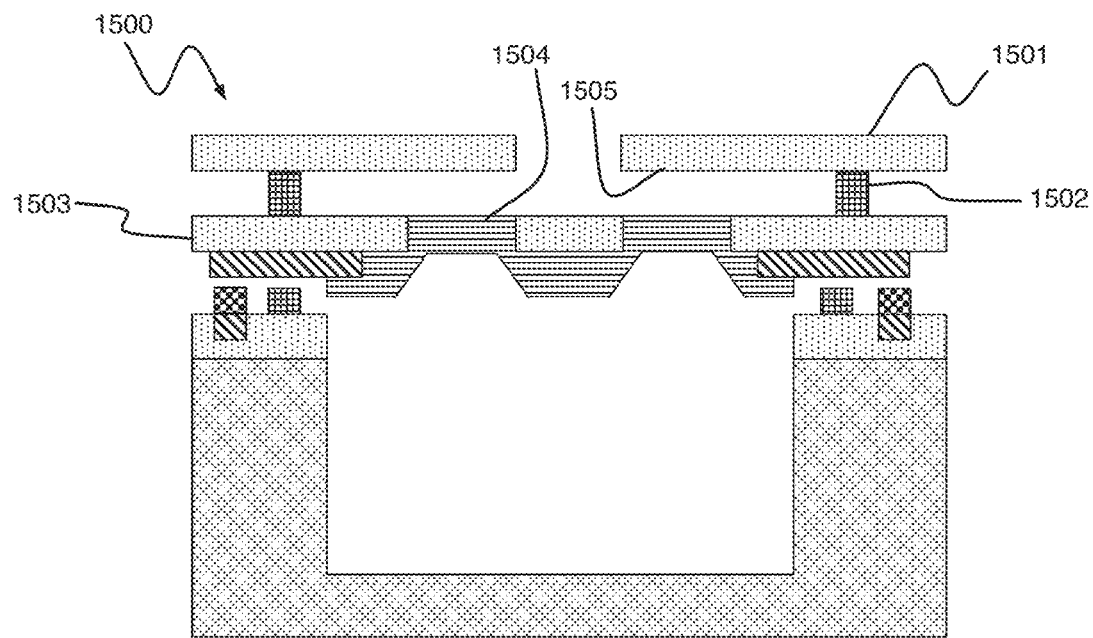
FIG. 15 is a cross section of the digital biomedical device comprising a baffle structure, according to an exemplary embodiment of the present invention.

In one or more embodiments of the present invention, a baffle structure comprising a baffle 1501 and a spacer 1502 is formed on a lid 1503 including a composite membrane 1504 of a digital biomedical device 1500 as shown in FIG. 15. The baffle structure controls a path of an active agent and collects residual reactive metal on a lower surface 1505.

Exemplary embodiments of the present invention can be associated with a variety of improvements including placement of the device at/near a treatment site, delivery on demand (e.g., emergency administration, pulsatile, adjustable continuous), automated delivery of single/multiple active agents and dosing in response to physiological and diagnostic feedback, patient compliance, low impact on patient lifestyle, low power parameters (e.g., current, ignition temperature), and small onboard power supply or wireless power parameters.

The methodologies of embodiments of the disclosure may be particularly well-suited for use in an electronic device or alternative system. Accordingly, embodiments of the present invention may take the form of an entirely hardware embodiment or an embodiment combining software and hardware aspects that may all generally be referred to herein as a "processor," "circuit," "module" or "system."

Furthermore, it should be noted that any of the methods described herein can include an additional step of providing a digital biomedical device including a reactive metal structure. Further, a computer program product can include a tangible computer-readable recordable storage medium with code adapted to be executed to carry out one or more method steps described herein, including the provision of the system with the distinct software modules.

Figure 16:
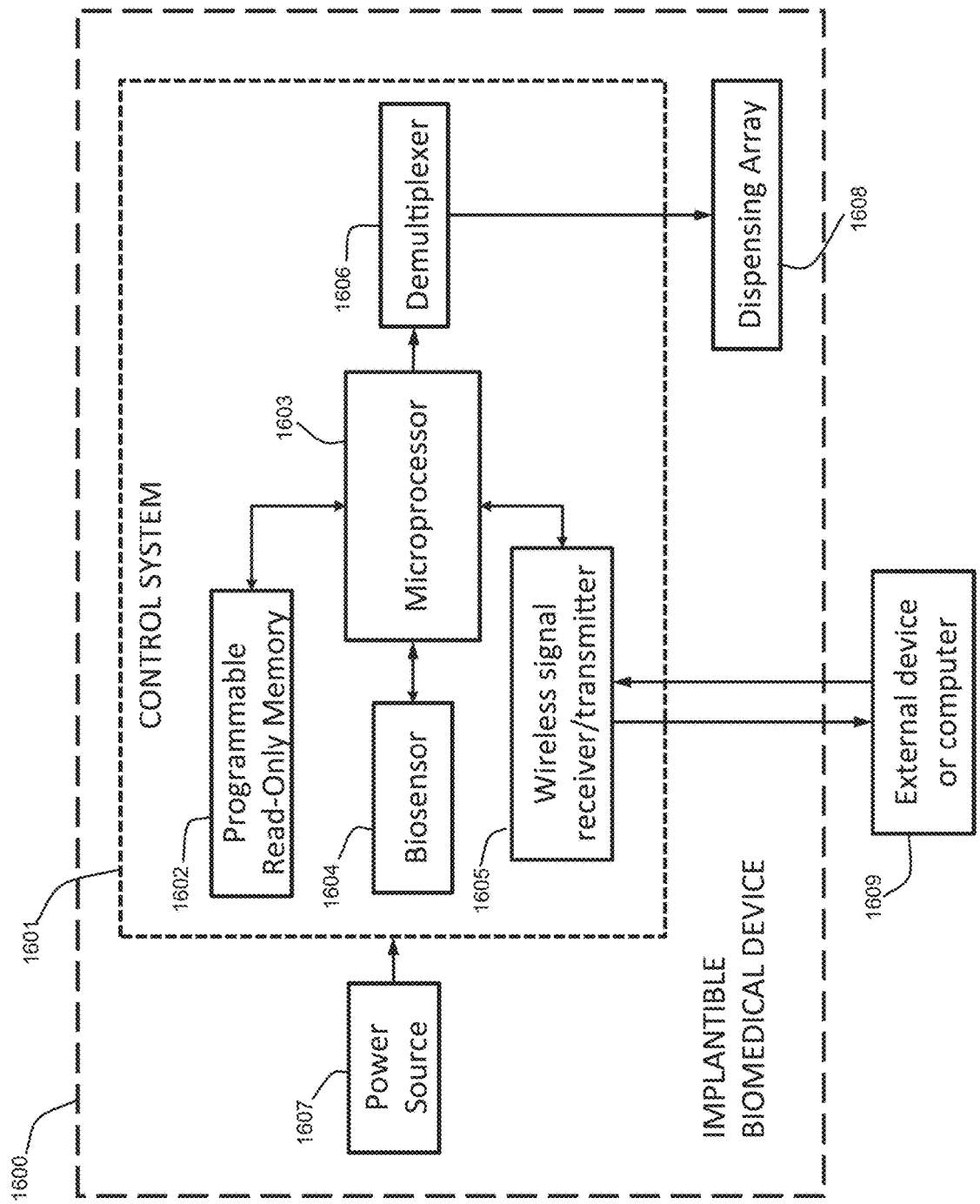
FIG. 16 is a diagram of a computer system configured to control a digital biomedical device according to an exemplary embodiment of the present invention.

Referring to FIG. 16; FIG. 16 is a block diagram depicting an exemplary computer system embodying the digital biomedical device 1600 according to an embodiment of the present invention. The computer system shown in FIG. 16 includes a control system 1601 having a memory 1602, a processor 1603, at least one sensor 1604, a communications device 1605 and an input/output device 1606. The control system 1601 is connected to a power supply 1607, a dispensing array 1608 and optionally, an external device or computer 1609.

In different applications, some of the components shown in FIG. 16 can be omitted. The whole system shown in FIG. 16 is controlled by computer readable instructions, which are generally stored in the memory 1602. The software can be downloaded from a network (not shown in the figures), stored in the memory 1602. Alternatively, software downloaded from a network (e.g., 1609) can be loaded into the memory 1602 and executed by the processor 1603 so as to complete the function determined by the software.

The processor 1603 may be configured to perform one or more methodologies described in the present disclosure, illustrative embodiments of which are shown in the above figures and described herein. Embodiments of the present invention can be implemented as a routine that is stored in memory 1602 and executed by the processor 1603 to process the signal from the sensor 1604. As such, the computer system is a general-purpose computer system that becomes a specific purpose computer system when executing routines of the present disclosure.

Although the computer system described in FIG. 16 can support methods according to the present disclosure, this system is only one example of a computer system. Those skilled of the art should understand that other computer system designs can be used to implement embodiments of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A digital biomedical device comprising:
   a substrate forming a cavity;
   a seal formed on the substrate and encircling the cavity;
   a lid coupled to the substrate by the seal, the lid comprising at least one via;
   a reactive metal structure comprising a plurality of metal layers, wherein the reactive metal structure is disposed in the at least one via of the lid;
   a metal trace configured to initiate a self-propagating reaction between the plurality of metal layers of the reactive metal structure and release contents of the cavity through the at least one via; and
   a power supply configured to apply an electric current to the metal trace.

2. The digital biomedical device of claim 1, wherein a thickness of each of the plurality of metal layers is between about 5 nanometers and about 50 nanometers.

3. The digital biomedical device of claim 1, wherein the reactive metal structure comprises a first layer of aluminum (Al) and a second layer of palladium (Pd).

4. The digital biomedical device of claim 1, wherein at least a portion of the lid comprises the reactive metal structure.

5. The digital biomedical device of claim 1, wherein the metal trace is a heater electrode.

6. The digital biomedical device of claim 1, wherein the self-propagating reaction of the reactive metal structure is initiated by electrical current passed through the reactive metal structure via the metal trace.

7. The digital biomedical device of claim 1, wherein the reactive metal structure is configured to fracture upon the application of the electric current to the metal trace.

8. The digital biomedical device of claim 1, wherein the lid is a composite structure containing at least a portion of the reactive metal structure and a non-reactive support structure, and wherein the reactive metal structure is a sacrificial material, removed during the self-propagating reaction.

9. The digital biomedical device of claim 8, wherein the composite structure is configured to become a porous structure upon the application of the electric current to the metal trace.

10. The digital biomedical device of claim 8, wherein a baffle structure is disposed outside the composite structure, and is configured to block the reactive metal structure from exiting the digital biomedical device following the self-propagating reaction.

11. The digital biomedical device of claim 1, wherein the lid is mechanically stressed and configured to peel upon the application of the electric current to the metal trace.

12. The digital biomedical device of claim 1, wherein the self-propagating reaction is initiated by a heater electrode.

13. The digital biomedical device of claim 1, wherein the reactive metal structure is configured to melt upon initiation of the self-propagating reaction.

14. The digital biomedical device of claim 1, wherein the reactive metal structure is configured to compromise the seal upon initiation of the self-propagating reaction.

* * * * *